(12) United States Patent
Davis et al.

(10) Patent No.: US 8,608,706 B2
(45) Date of Patent: Dec. 17, 2013

(54) ADHESIVE TAPE FOR AN INTRAVASCULAR CATHETER

(75) Inventors: Mable C. Davis, Decatur, IL (US); Gail S. Hesse, Oreana, IL (US); Jeania M. Kitchens, Oreana, IL (US)

(73) Assignee: Majorus Medical, Inc., Decatur, IL (US)

( * ) Notice: Subject to any disclaimer, the term of this patent is extended or adjusted under 35 U.S.C. 154(b) by 510 days.

(21) Appl. No.: 12/477,540

(22) Filed: Jun. 3, 2009

(65) Prior Publication Data

US 2009/0240207 A1    Sep. 24, 2009

Related U.S. Application Data

(60) Continuation of application No. 11/342,958, filed on Jan. 30, 2006, now Pat. No. 7,544,186, which is a division of application No. 11/154,869, filed on Jun. 16, 2005, now Pat. No. 7,524,307.

(60) Provisional application No. 60/583,565, filed on Jun. 28, 2004, provisional application No. 60/685,347, filed on May 27, 2005.

(51) Int. Cl.
*A61M 25/02* (2006.01)

(52) U.S. Cl.
USPC ............................................. 604/180; 604/174

(58) Field of Classification Search
USPC ............ 604/180, 386, 389, 174; 128/DIG. 26
See application file for complete search history.

(56) References Cited

U.S. PATENT DOCUMENTS

| | | | |
|---|---|---|---|
| 4,413,621 A | 11/1983 | McCracken | 602/52 |
| 4,460,356 A | 7/1984 | Moseley | 604/180 |
| 4,490,141 A | 12/1984 | Lacko et al. | 604/180 |
| 4,614,183 A * | 9/1986 | McCracken et al. | 128/846 |
| 4,646,731 A | 3/1987 | Brower | 606/215 |
| 4,822,342 A | 4/1989 | Brawner | 604/180 |
| 4,838,868 A | 6/1989 | Forgar et al. | 604/180 |
| 5,087,248 A | 2/1992 | Beisang, III | 604/180 |
| 5,098,399 A | 3/1992 | Tollini | 604/180 |
| 5,213,565 A * | 5/1993 | Rollband | 602/41 |
| 5,219,336 A | 6/1993 | Wilk | 604/180 |
| 5,232,453 A | 8/1993 | Plass | 604/180 |
| 5,480,719 A | 1/1996 | Tollini | 428/345 |
| 5,546,938 A | 8/1996 | McKenzie et al. | 128/207.17 |
| 6,302,867 B1 | 10/2001 | Brown et al. | 604/174 |

(Continued)

FOREIGN PATENT DOCUMENTS

FR    2 697 756 A    5/1994

*Primary Examiner* — Laura Bouchelle
(74) *Attorney, Agent, or Firm* — Alvin T. Rockhill

(57) ABSTRACT

The present invention discloses an adhesive tape to secure an intravascular catheter to the skin of a patient at an intravascular site comprising: (a) a strip of tape having adhesive on all of one side except for portions at the ends, the strip of tape having a length of about 15 mm to about 300 mm and width of about 4 mm to about 30 mm; (b) two removable covers affixed near the ends of the adhesive side of the strip, wherein the removable covers are separated from each other by a centrally located portion of the strip of tape; and (c) a third removable cover affixed to the central portion of the adhesive side of the strip of tape. The subject invention further reveals a sterile intravascular starter kit, said kit being comprised of the adhesive tape for an intravascular catheter, a tourniquet, a gauze pad, an antiseptic skin preparation device, optionally a towel, and a clear occlusive dressing.

7 Claims, 7 Drawing Sheets

(56) References Cited

U.S. PATENT DOCUMENTS

| | | | |
|---|---|---|---|
| 6,551,285 B1 | 4/2003 | Bierman | 604/180 |
| 6,827,706 B2 | 12/2004 | Tollini | 604/180 |
| 7,524,307 B2 * | 4/2009 | Davis et al. | 604/180 |
| 2002/0195114 A1 | 12/2002 | Tollini | 604/180 |
| 2003/0028148 A1 | 2/2003 | Hampton | 604/180 |

* cited by examiner

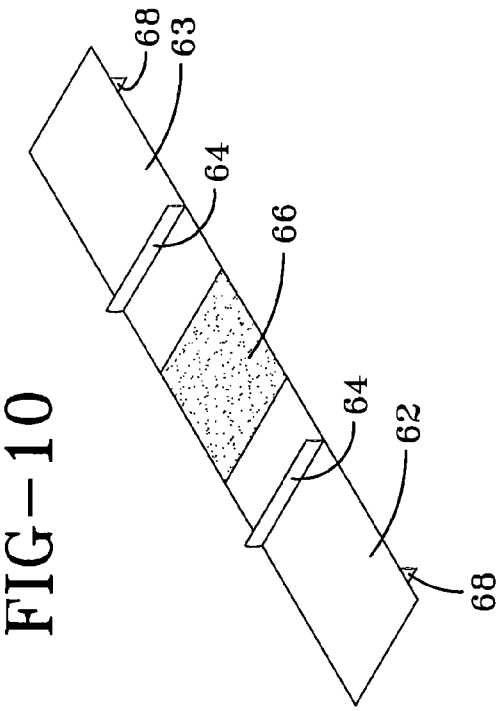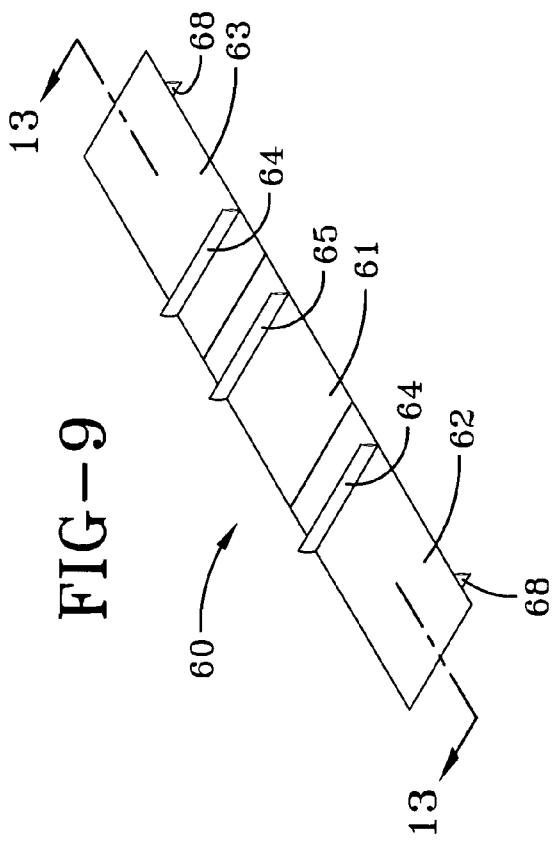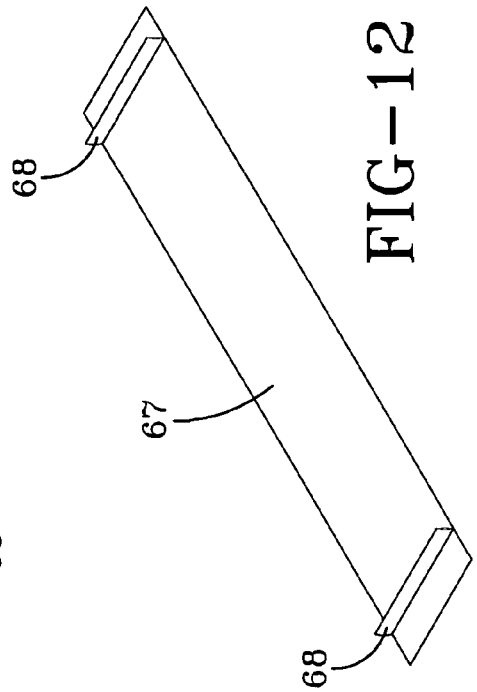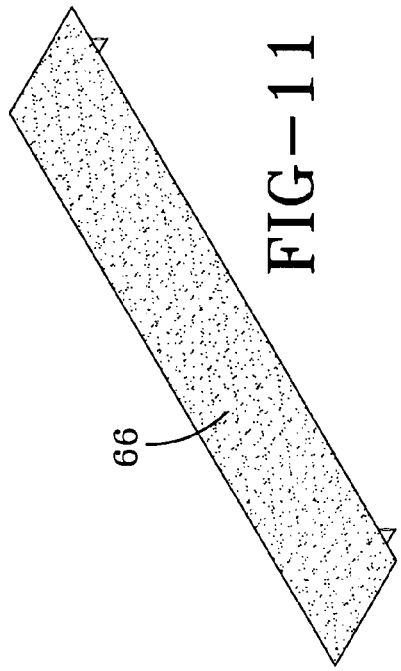

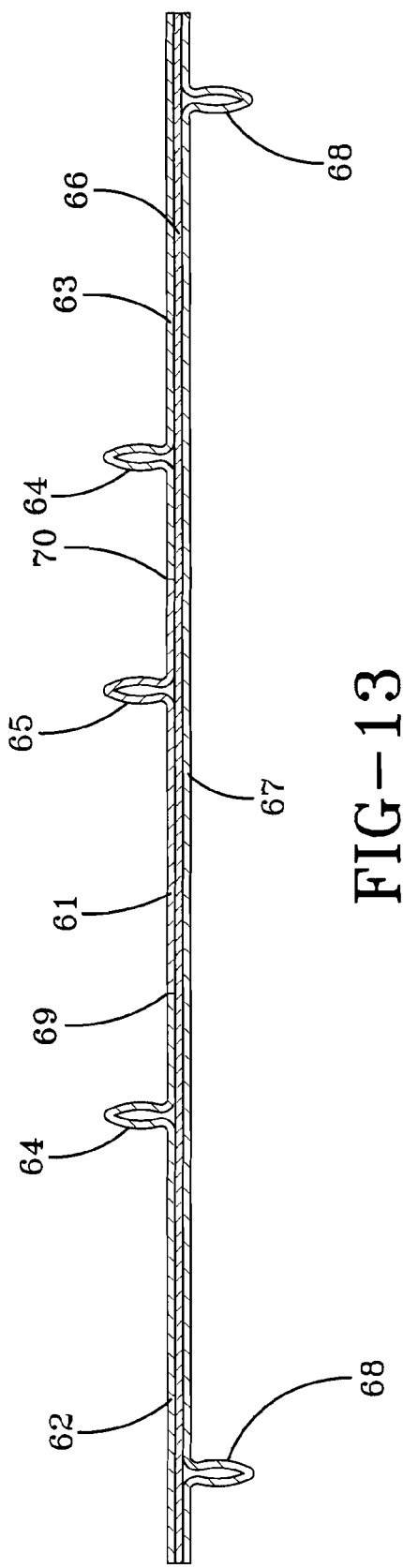

ADHESIVE TAPE FOR AN INTRAVASCULAR CATHETER

This application is a continuation of U.S. patent application Ser. No. 11/342,958, filed on Jan. 30, 2006, which is a divisional and a continuation-in-part of U.S. patent application Ser. No. 11/154,869, filed on Jun. 16, 2005, which claims the benefit of U.S. Provisional Patent Application Ser. No. 60/583,565 filed on Jun. 28, 2004, and U.S. Provisional Patent Application Ser. No. 60/685,347 filed on May 27, 2005. This patent application incorporates the teachings of U.S. patent application Ser. No. 11/342,958, U.S. patent application Ser. No. 11/154,869, U.S. Provisional Patent Application Ser. No. 60/583,565, and U.S. Provisional Patent Application Ser. No. 60/685,347 herein by reference in their entirety.

FIELD OF THE INVENTION

This invention relates to intravascular catheters. More particularly, this invention relates to an intravascular catheter adhesive tape for affixing the catheter to an intravascular site on the skin of a human or animal patient.

BACKGROUND OF THE INVENTION

Intravascular catheters are used to supply liquids directly into a patient's bloodstream. An intravascular catheter consists of a flexible tube attached to a hollow plastic hub. An intravascular catheter is typically inserted using an integral stylet. A stylet is a hollow metal needle that fits within and extends beyond the flexible tube of the catheter. The stylet is used to puncture the patient's skin and enter the blood vessel. After the stylet is inserted through the skin into the patient's blood vessel, it is removed to leave only the flexible tube within the blood vessel. The hub is then secured to the patient's body before it is connected to a source of liquids.

A conventional procedure for securing the intravascular catheter is shown in FIGS. 1 to 4. Referring to FIG. 1, a conventional intravascular catheter 10 comprises a tube 11, a hub 12, two wings 13, and a port 14 for connection to a liquid reservoir. However, some intravascular catheters do not include wings. Referring to FIG. 2, the intravascular catheter is inserted into the back of the hand of a patient 20. A strip of adhesive tape 30 that has been previously torn from a roll is then placed underneath the intravascular catheter with the adhesive side facing up. Referring to FIG. 3, the next step is to fold one side of the tape over so the adhesive side makes contact with the patient's skin. Some medical professionals cross the tape over at an angle to the hub as shown while others fold it over parallel to the hub. Referring to FIG. 4, the next step is to fold the other side of the tape over. Again, some medical professionals fold the other side parallel to the hub. The final step is to place a cover over the catheter and the tape.

A variety of other catheters and tubes in the medical field are secured in the same way, including nasogastric tubes, urinary catheters, intrauterine pressure catheters, central venous lines, and the like. It is understood that the term intravascular catheter refers to this general class of the catheters and tubes that are conventionally secured to the patient's body with adhesive tape.

There are several disadvantages associated with the conventional method of securing the intravascular catheter. First, the medical professional should, but does not always, wear latex or latex-free gloves during the process. Handling adhesive tape is very difficult when wearing gloves. Second, there are several risks of contamination. The use of a single roll of adhesive tape by different medical professionals and on different patients presents one risk. An even greater risk arises because medical professionals typically tear off a strip of tape and stick it temporarily on a nearby surface before inserting the intravascular catheter. The strip of tape is then retrieved for use. The strip carries with it contamination from the surface. The problem of contamination is widely recognized in the medical profession. See, for example, "Guidelines for the Prevention of Intravascular Catheter-Related Infections" published in the Aug. 9, 2002, edition of the *Morbidity and Mortality Weekly Report* of the Center for Disease Control.

Because of the disadvantages associated with the conventional method of securing the intravascular catheter with conventional adhesive tape, a number of specialized products have been disclosed for holding intravascular catheters. For example, Lacko et al., U.S. Pat. No. 4,490,141, issued Dec. 25, 1984, discloses an adhesive device having a slot, a hole, and a hingedly connected portion. The device has three cover sheets that are sequentially removed when using the device. Beisang, III, U.S. Pat. No. 5,087,248, issued Feb. 11, 1992, discloses an adhesive patch having four covers that are sequentially removed when using the device. The Lacko et al. device and the Beisang, III device contain cover sheets that have the same shape and size as the adhesive strips, making it very difficult to remove them while wearing gloves. The Lacko et al. device and the Beisang, III device also must be precisely oriented relative to the IV tube.

Accordingly, a demand exists for an intravascular catheter adhesive device that can be easily used by a medical professional wearing latex or latex-free gloves and that reduces the risk of contamination. There is also a need for an easier, faster and less irritating way for removing catheters which are taped to the skin of a patient.

SUMMARY OF THE INVENTION

The goal of this invention is to provide an improved intravascular catheter adhesive tape. The intravascular catheter adhesive tape of this invention can easily be used by a medical professional wearing latex or latex-free gloves. The intravascular catheter adhesive tape securely holds an intravascular catheter in place and reduces the risk of contamination. The adhesive tape of this invention also offers a simpler, quicker and gentler way for removing catheters which are taped to the skin of a patient.

The present invention more specifically discloses an adhesive tape to secure an intravascular catheter to the skin of a patient at an intravascular site comprising: (a) a strip of tape having adhesive on all of one side, the strip of tape having a length of about 15 to about 300 mm and width of about 4 to about 30 mm; (b) two removable covers affixed near the ends of the adhesive side of the strip, wherein the removable covers are separated from each other by a centrally located portion of the strip of tape; (c) a third removable cover affixed to the central portion of the adhesive side of the strip of tape; (d) a first tab affixed near one end of the non-adhesive side of the strip; and (e) a second tab affixed near the other end of the non-adhesive side of the strip.

The present invention also specifically discloses an adhesive tape to secure an intravascular catheter to the skin of a patient at an intravascular site comprising: (a) a strip of tape having adhesive on all of one side except for portions at the ends, the strip of tape having a length of about 15 to about 300 mm and width of about 4 to about 30 mm; (b) two removable covers affixed near the ends of the adhesive side of the strip, wherein the removable covers are separated from each other by a centrally located portion of the strip of tape; and (c) a third removable cover affixed to the central portion of the adhesive side of the strip of tape.

The adhesive tape of this invention comprises: (a) a strip of tape having adhesive on all of one side except for portions at the ends, the strip of tape having a length of about 50 to 150 mm and width of about 5 to 20 mm; (b) two removable covers affixed near the ends of the adhesive side of the strip, the covers overhanging the non-adhesive portions at the ends of the strip and overhanging the sides of the strip and being separated from each other such that a centrally located portion of the adhesive is exposed; and (c) a third removable cover affixed to the central portion of the adhesive side of the strip, the cover overhanging the two removable covers and overhanging the sides of the strip.

The present invention also further discloses a sterile intravascular starter kit, said kit being comprised of an adhesive tape for an intravascular catheter, a tourniquet, a gauze pad, an antiseptic skin preparation device, and a clear occlusive dressing, wherein the adhesive tape for the intravascular catheter comprises: (a) a strip of tape having adhesive on at least a portion of one of its side, the strip of tape having a length of about 15 to about 300 mm and width of about 4 to about 30 mm; (b) two removable covers affixed near the ends of the adhesive side of the strip, wherein the removable covers are separated from each other by a centrally located portion of the strip of tape; and (c) a third removable cover affixed to the central portion of the adhesive side of the strip of tape.

BRIEF DESCRIPTION OF THE DRAWINGS

FIG. 9 is a perspective view of the preferred embodiment of the adhesive side of the intravascular catheter adhesive tape of this invention with all three removable covers in place.

FIG. 10 is a perspective view of the preferred embodiment of the adhesive tape of this invention with the third removable cover removed.

FIG. 11 is a perspective view of the preferred embodiment of the adhesive tape with the first and second removable covers removed.

FIG. 12 is a perspective view of the non-adhesive side of the preferred embodiment of the adhesive tape with all three removable covers in place.

FIG. 13 is a cross-sectional view of the adhesive tape of this invention.

DETAILED DESCRIPTION OF THE INVENTION

Figure 1:
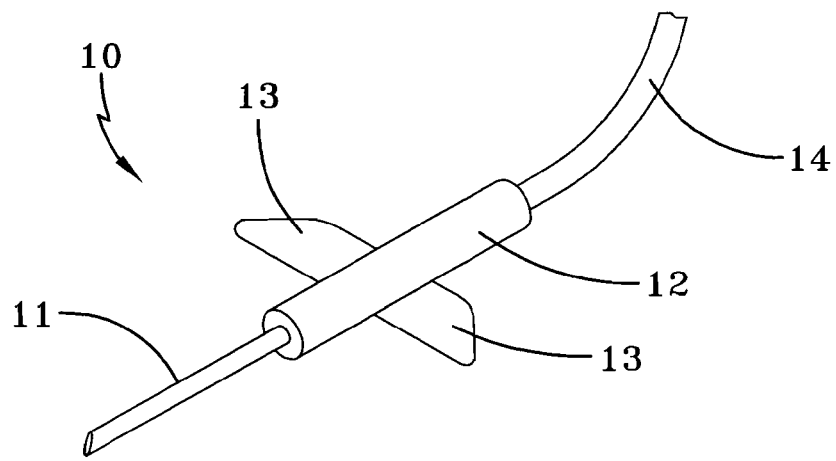
FIG. 1 is a perspective view of a prior art intravascular catheter.
Figure 2:
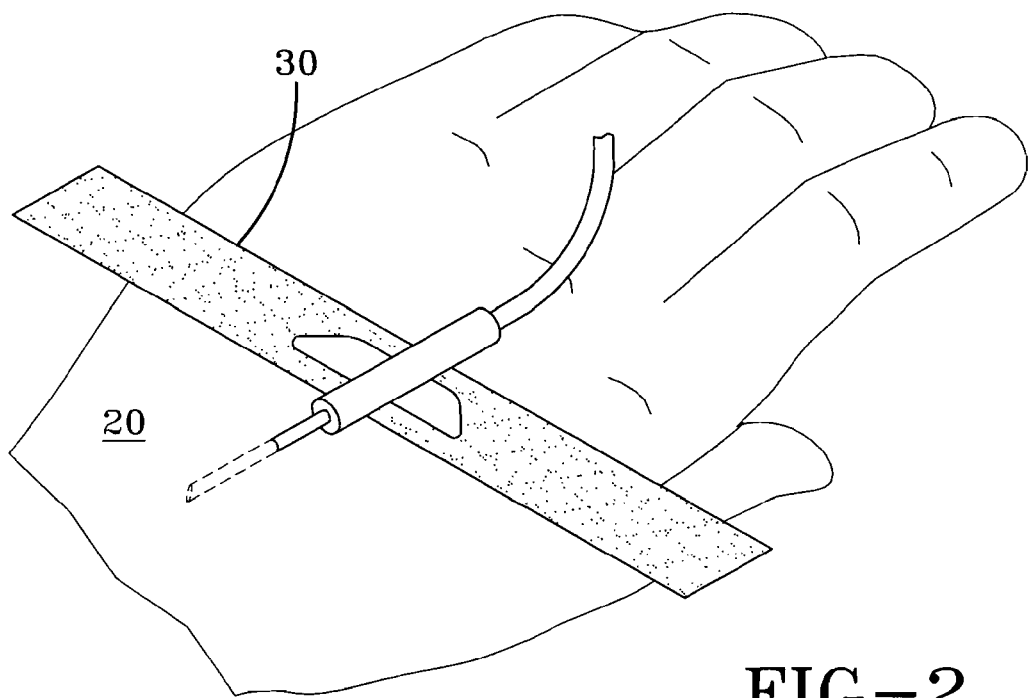
FIG. 2 is a perspective view of a first step in the catheter being secured to a patient.
Figure 3:
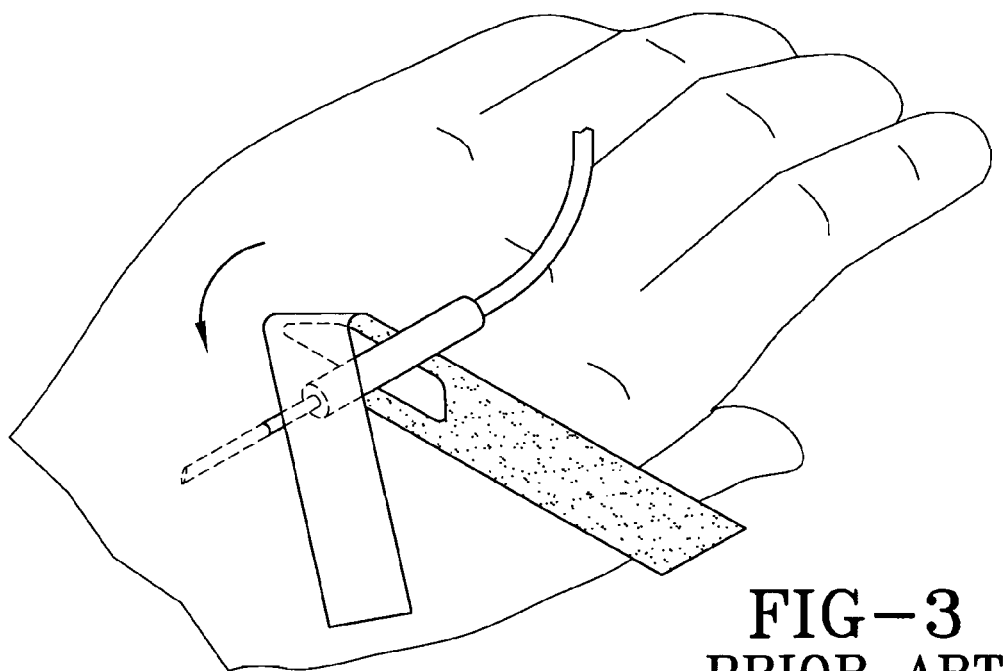
FIG. 3 is a perspective view of a second step in the catheter being secured to a patient.
Figure 4:
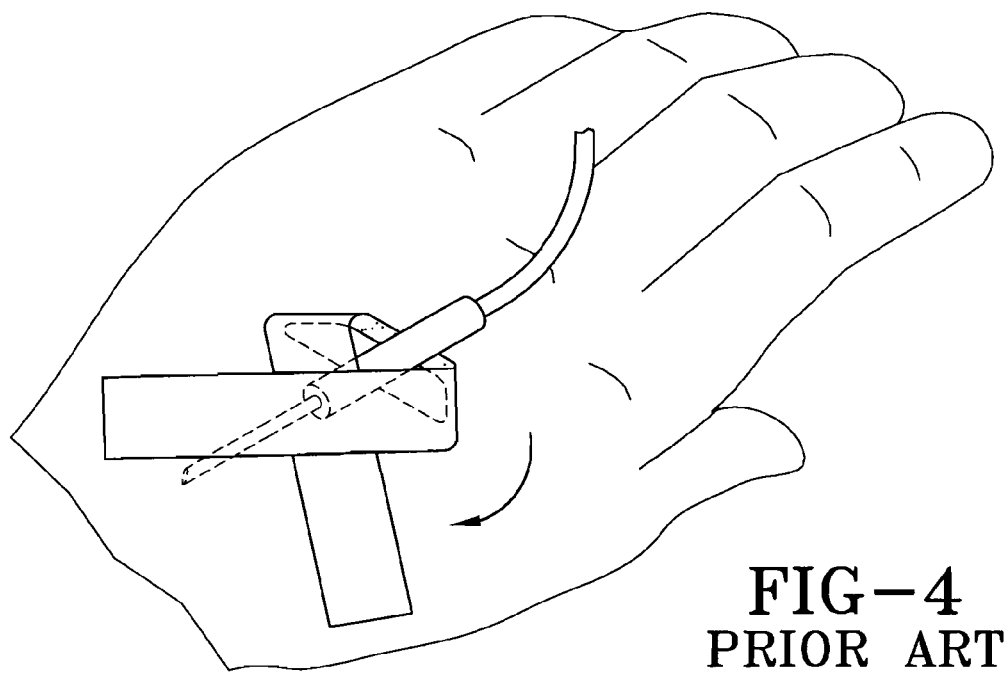
FIG. 4 is a perspective view of a third step in the catheter being secured to a patient.
Figure 5:
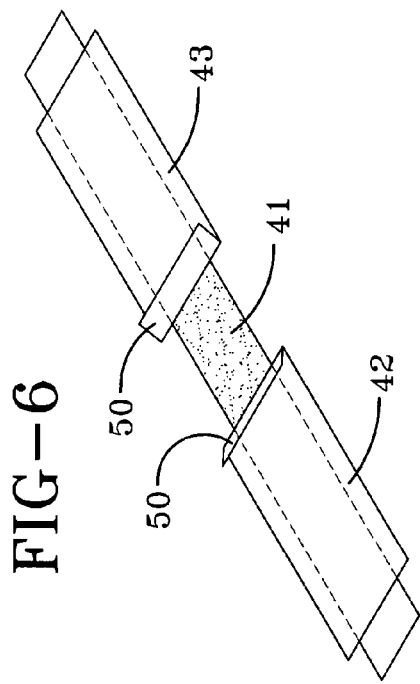
FIG. 5 is a perspective view of the adhesive side of the intravascular catheter adhesive tape of this invention with all three removable covers in place.
Figure 6:
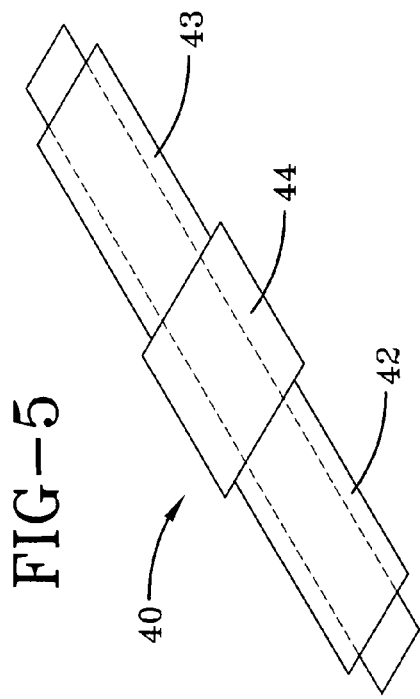
FIG. 6 is a perspective view of the intravascular catheter adhesive tape of this invention with the third removable cover removed.
Figure 7:
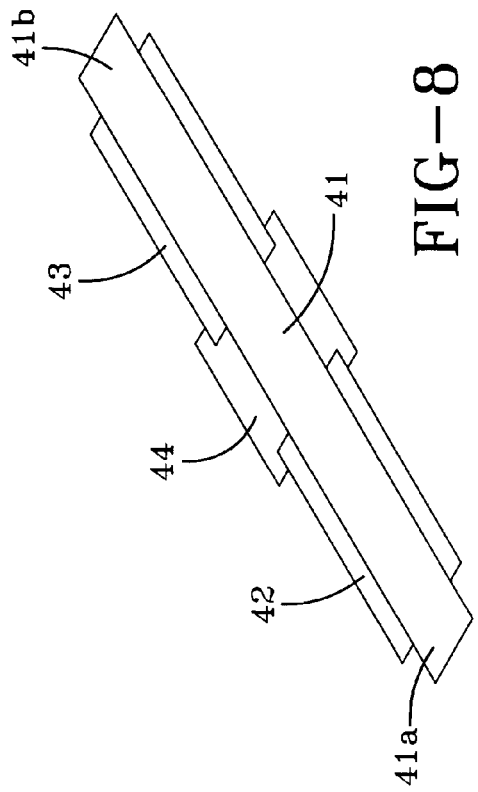
FIG. 7 is a perspective view of the intravascular catheter adhesive tape of this invention with the first and second removable covers removed.
Figure 8:
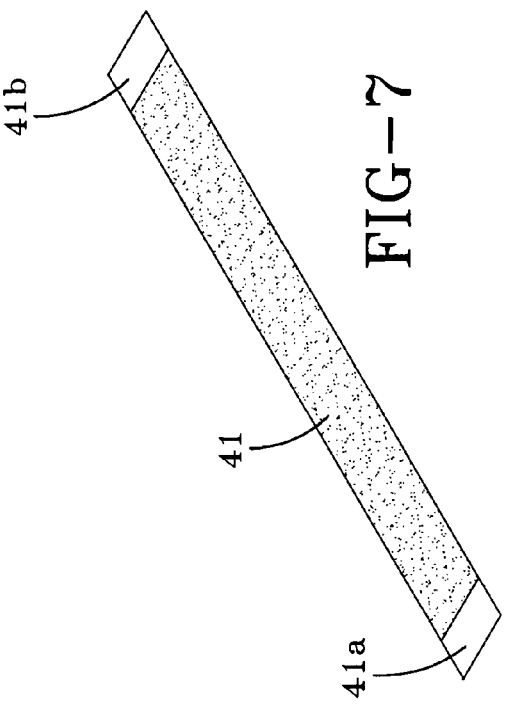
FIG. 8 is a perspective view of the non-adhesive side thereof with all three removable covers in place.

This invention is best understood by reference to the drawings. The intravascular catheter adhesive tape 40 of this invention is shown in FIGS. 5 through 8. The adhesive tape comprises a strip of tape 41 having adhesive on one side with two removable end covers 42 and 43 affixed near the ends of the adhesive side and a third removable center cover 44 affixed to the central portion of the adhesive side. The adhesive side of the tape is shown in FIGS. 5 through 7 and the non-adhesive side of the tape is shown in FIG. 8. The components of the intravascular catheter adhesive tape are discussed in detail below.

The strip of tape 41 has an adhesive on one of its sides and is non-adhesive on the other side. In one embodiment of this invention adhesive covers the entire surface of one side of the tape. However, the adhesive is preferably on only a portion of one side of the tape with a small area at each end of the tape being free of exposed adhesive. As best seen in FIG. 7, most of the side is adhesive as represented by the dotted area. The two ends of the tape 41a and 41b are not adhesive. These ends either lack adhesive or have non-removable covers on top of adhesive. In either case in this preferred embodiment of the invention adhesive is not present on the surface of the tape 41 (even after the removable end covers have been removed from the tape). The length of the non-adhesive portions of the tape 41a and 41b is not particularly critical so long as the length of the non-adhesive portion is great enough for a healthcare professional to grip the end of the tape after it has been affixed to the skin of a patient. However, the two non-adhesive ends of the tape 41a and 41b typically have a length of about 2 mm to about 15 mm and more typically have a length of about 5 mm to about 12 mm. The material of the tape and the type of adhesive are not critical. Conventional plastics and fabrics are suitable and conventional adhesives are also suitable. The strip generally has a length of about 15 mm to 300 mm, preferably has a length of about 20 mm to 200 mm, and most preferably has a length of 50 mm to 150 mm. The strip normally has a width of about 4 mm to 50 mm, preferably has a width of about 4 mm to 25 mm, and most preferably has a width of 5 mm to 10 mm.

Two removable end covers 42 and 43 are affixed near the ends of the adhesive side of the strip. The material of the covers is not critical. Conventional plastics and papers are suitable. The end covers can optionally overhang the non-adhesive portions of the strip by about 5 mm and optionally overhang the sides of the strip by about 1 mm to 3 mm. The end covers are generally separated by about 10 mm to 15 mm so that a centrally located portion of the adhesive can be exposed by removal of the removable center cover 44. The end covers are typically separated by a length that is between 2% and 33% of the overall length of the adhesive tape 40. The end covers are more typically separated by a length that is between 10% and 20% of the overall length of the adhesive tape 40. As best seen in FIG. 6, the inner ends of the covers are preferably folded back to form cover tabs 50 for ease of gripping after the center cover has been removed.

The center cover 44 is affixed to the central portion of the adhesive side of the strip. It optionally overhangs the end covers by about 5 mm so that it can be removed first without dislodging the end covers. The center cover can be made of the same type of materials as the end covers. The center cover optionally overhangs the sides of the strip by about 2 to 5 mm, preferably slightly more than the end covers.

In another embodiment of this invention, the removable covers are designed in a manner where they do not overhang the sides of the strip. This embodiment of the invention is depicted in FIG. 9, FIG. 10, FIG. 11 and FIG. 12. In this embodiment of the invention, tabs are affixed to the removable covers for easy removal from the adhesive side of the strip eliminating the need for the removable covers to overhang the sides of the strip. FIG. 9 shows tabs 64 which are affixed to the removable covers 63 affixed to the ends of the adhesive side of the tape. Tab 65 is shown as being affixed to the central cover 61 which is shown as covering the centrally located portion of the adhesive side of the strip. FIG. 10 shows the adhesive side of the strip after the center cover 61 has been removed exposing the adhesive 66 located in the center of the strip. Tabs 64 can be grasped by the healthcare provider to remove the removable cover 62 and removable cover 63 covering the adhesive at the two opposite ends of the strip. After end cover 62 and end cover 63 have been removed, the adhesive 66 is exposed on the entire adhesive side of the strip as depicted in FIG. 11. The non-adhesive portion of the strip which is on the opposite side of the tape from the adhesive portion is depicted in FIG. 12. In this embodiment of the invention, the adhesive covers the entire length of the adhesive side of the tape. In this case, tabs 68 are affixed to each end of the non-adhesive side of the tape 67 to facilitate easy removal by the healthcare provider at the time that the catheter is removed from the injection site.

FIG. 13 is a cross-sectional view depicting this embodiment of the invention. In FIG. 13, the non-adhesive side of the tape 67 is shown with tabs 68 located near the ends of the tape for easy removal. In this cross-sectional view of the tape, the adhesive 66 is sandwiched between the non-adhesive side of the tape 67 and the centrally located removable cover 61, and the removable covers 62 and 63 located at the ends of the tape. A first tab 64 and a second tab 65 are affixed to the removable covers to facilitate easy removal.

It should be noted that removable cover 62 abuts the centrally located removable cover 61 at abutment point 69 so that the adhesive is completely covered. The other end of the centrally located removable cover 61 is abutted by removable cover 63 at a second abutment point 70.

Figure 14:
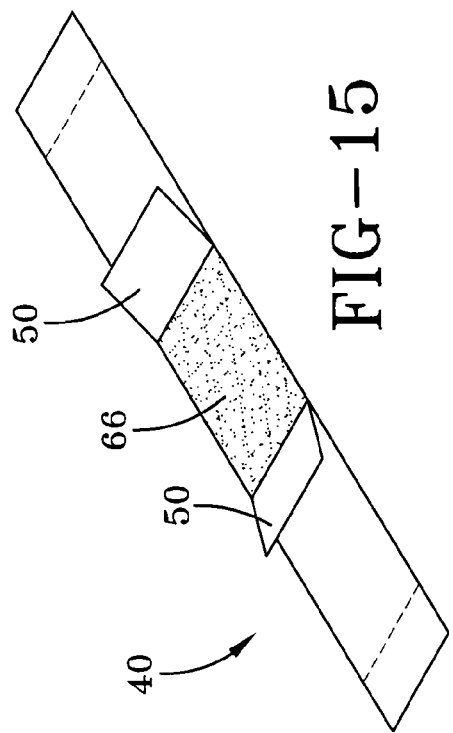
FIG. 14 is a perspective view of a highly preferred embodiment of the adhesive side of the intravascular catheter adhesive tape of this invention with all three removable covers in place.
Figure 15:
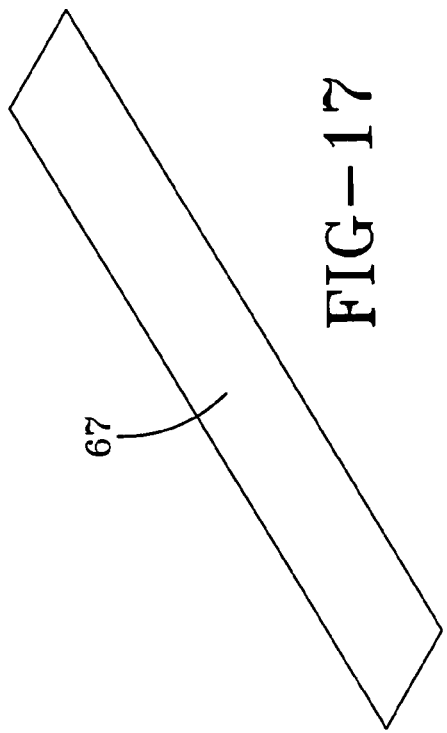
FIG. 15 is a perspective view of a highly preferred embodiment of the intravascular catheter adhesive tape of this invention with the third removable cover removed.

In another highly preferred embodiment of this invention, the removable covers are designed in a manner where they do not overhang the sides of the strip. This embodiment of the invention is depicted in FIG. 14, FIG. 15, FIG. 16, FIG. 17, and FIG. 18. As can be seen in FIG. 14, in this embodiment of the invention, center cover 61 is long enough to extend over end cover 62 and end cover 63 to the extent that the tabs 71 are easy to grasp to remove the center cover 61 from the tape. In this embodiment of invention the center cover 61 will preferably overhang the end covers by at least about 3 mm so that it can be removed first without dislodging the end covers. For instance, the center cover 61 can overhang the end covers by 4 mm to 25 mm and will preferably overhang the end covers by 5 mm to 15 mm. It is typically most preferred for the center cover 61 to overhand end cover 62 and end cover 63 by 8 mm to 12 mm. After the center cover 61 is removed, the adhesive 66 is exposed in the center portion of the tape as shown in FIG. 15.

Figure 16:
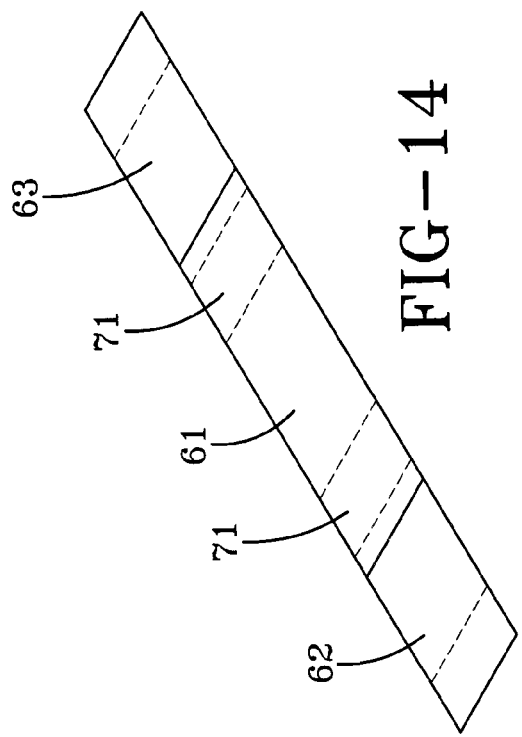
FIG. 16 is a perspective view of a highly preferred embodiment of the intravascular catheter adhesive tape of this invention with the first and second removable covers removed.
Figure 17:
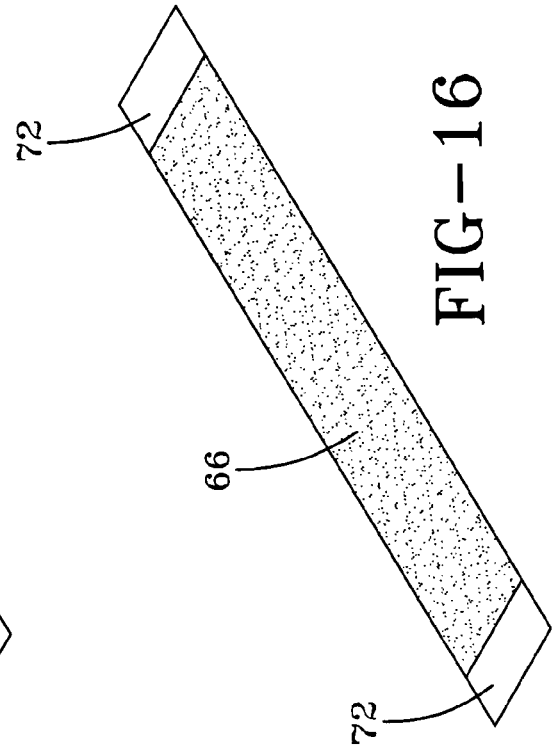
FIG. 17 is a perspective view of a highly preferred embodiment of the non-adhesive side thereof.

After the removable center cover 61 is removed and the adhesive 66 is exposed, removable end cover 62 and removable end cover 63 can then be easily removed by grasping cover tabs 50 which are typically simply a portion of removable end cover 62 and removable end cover 63 which are folded back toward the ends of the adhesive tape 40. At each end of the adhesive tape 40 a non-adhesive tab 72 can be applied over the adhesive 66 as shown in FIG. 16 to allow for the tape to be easily removed from the skin of the patient at the time that the catheter is ultimately removed. These non-adhesive tabs 72 are typically a thin sheet made of paper, plastic, or fabric that will adhere to the adhesive and prevent the adhesive from sticking to other objects, such as a patient's skin, a health provider's gloves, or other foreign objects. As has already been explained, the tape can also optionally be manufactured in a manner whereby the adhesive 66 is simply not applied to the ends of the tape (see 41a and 41b in FIG. 7). In this highly preferred embodiment of the invention the non-adhesive side of the tape 67, as shown in FIG. 17, is essentially a continuous strip of plastic, fabric or paper that does not have any exposed adhesive on its surface.

Figure 18:
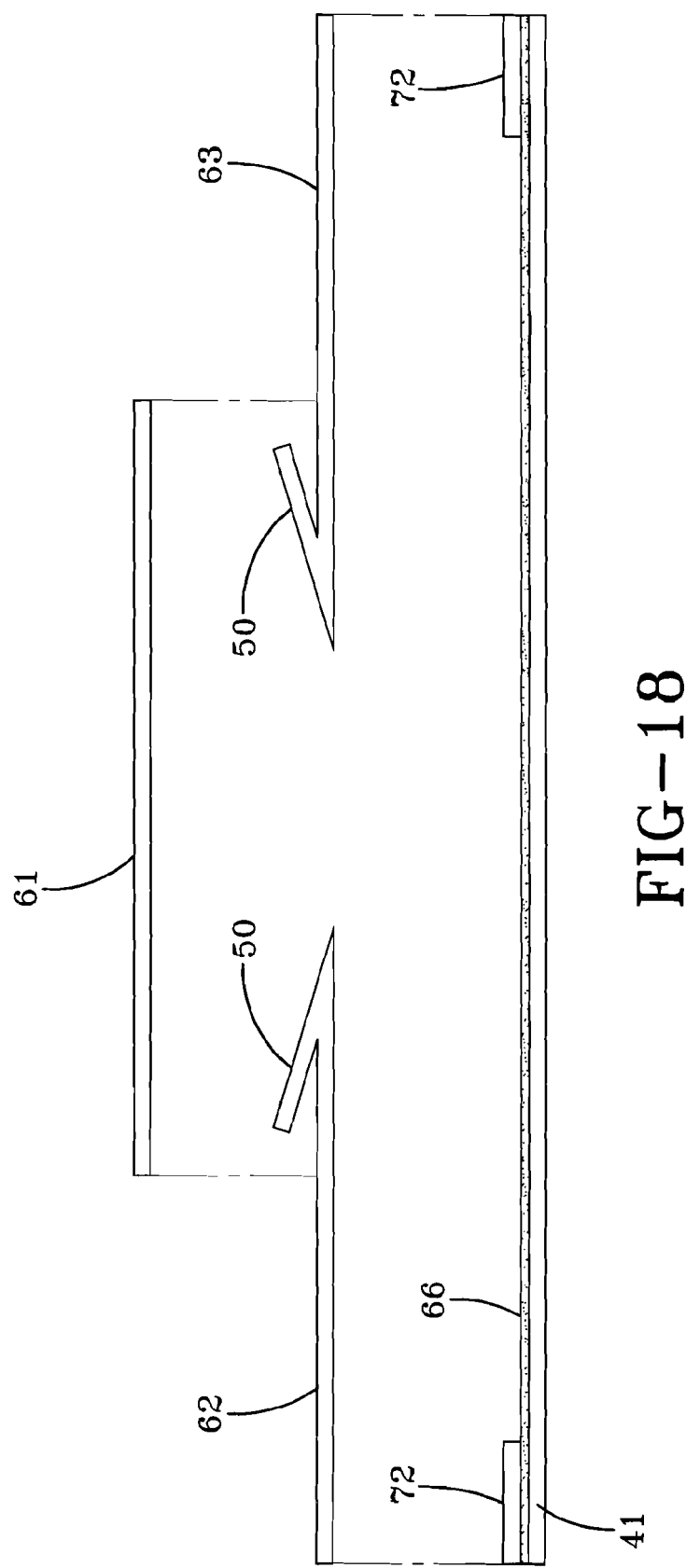
FIG. 18 is an exploded side view of a highly preferred embodiment of the adhesive tape of this invention with all three removable covers in place.

The design of this highly preferred embodiment of this invention is also illustrated in FIG. 18 which is an exploded side view of the intravascular catheter adhesive tape. As can be seen from FIG. 18 the adhesive 66 is applied onto a base strip of tape 41. The base strip of tape will typically be a continuous plastic film, fabric, or paper that has sufficient tensile strength to provide the adhesive tape with the required physical properties. For instance, the base strip can optionally be an extruded plastic film or a plastic film of biaxial orientation. Non adhesive tabs 72 are applied directly to the adhesive layer 66 to cover all of the adhesive located at the ends of the tape. Removable end cover 62 and removable end cover 63 are applied at the ends of the tape to cover the non-adhesive tabs 72 and the adhesive 66 so as to leave only the adhesive located in the center of the tape exposed. Removable end covers 62 and removable end covers 63 are folded back upon themselves to form cover tabs 50. The adhesive 66 located in the center portion of the tape is covered with removable center cover 61 which covers the adhesive 66 located in the center portion of the tape and also extends over cover tabs 50 so that removable center cover 61 can be easily grasped and removed without disturbing end cover 62 or end cover 63.

The use of the intravascular catheter adhesive tape can now be considered. After an intravascular catheter is inserted into the patient, the adhesive tape is held with the adhesive side facing up (away from the patient). The center cover is removed and the adhesive tape is centered under the hub of the catheter so that the exposed adhesive is directly below the hub. The hub is gently pressed down against the exposed adhesive. One of the end covers is then removed and that end of the tape is folded over the catheter. The other end cover is then removed and that end of the tape is folded over the catheter.

The covers are easy to grasp by a medical professional wearing gloves. This is by virtue of the fact that the covers are equipped with tabs or overhang the sides of the tape, in either case making it easy for the healthcare provider to grasp and remove the covers from the tape. More importantly, the adhesive tape of this invention eliminates the need to temporarily stick the tape to a potentially contaminated surface prior to being used to affix the catheter to an intravascular site on the skin of a patient. Since there is no need to bring the adhesive tape into contact with a contaminated surface, the risk of catheter-related nosocomial infection is greatly reduced. The adhesive tape of this invention also eliminates any temptation that a healthcare provider may have to use his or her bare hands in affixing the catheter to an intravascular site because the adhesive tape of this invention can be easily used wearing gloves. This protects both the patient and the healthcare provider from potential risk. Also, a catheter can be secured to the skin of a patient utilizing the adhesive tape of this invention with only one hand which offers the advantage of leaving the healthcare provider with a "free" hand to stabilize the catheter at the intravascular site.

The adhesive tape of this invention can also be easily removed from a patient by virtue of the fact that it can be easily and firmly grasped by a healthcare provider for removal. This is advantageous in that the medical professional is not required to "dig" at the end or side of conventional tape to remove it from the skin. The digging action associated with removal of conventional tape is irritating to most patients and can be harmful to patients with fragile skin, such as the elderly and neonates. Since the adhesive tape of this invention has tabs that can be easily gripped for removal from the skin of the patient, the removal procedure is quicker and far less irritating.

This invention is illustrated by the following examples that are merely for the purpose of illustration and are not to be regarded as limiting the scope of the invention or the manner in which it can be practiced. Unless specifically indicated otherwise, parts and percentages are given by weight.

Comparative Example 1

Intravascular catheters are commonly inserted into a blood vessel on the back of a human patient's hand utilizing aseptic techniques. In such procedures, the healthcare provider typically wears gloves which are preferably sterile for both his or her protection and the protection of the patient. The first step of the process normally involves placing a sterile towel under the patient's arm or hand. Then, the healthcare provider sequentially tears several pieces of tape from a roll of tape in appropriate lengths for subsequent use in affixing the catheter to the intravascular site. As these strips of tape are torn from the roll of tape, the healthcare provider typically sticks the end of each of the strips to a convenient surface to allow the tape strips to hang so that they are accessible. This surface could be an I.V. pole, bed rail, bedside table or other convenient object nearby.

In the next step of the conventional procedure, a tourniquet is applied to the patient's arm. The healthcare provider then cleans and sterilizes the site where the catheter will be inserted into the patient with an antiseptic skin prep, such as an antiseptic swab. The antiseptic is allowed to dry. In such a procedure, an integral stylet is then inserted into a blood vessel on the back of the patient's hand by utilizing the sharp needle of the stylet to puncture through the patient's skin and other tissue to allow the stylet to enter the blood vessel. The needle is then removed from the patient's body while allowing the end of the intravascular catheter to remain in the blood vessel. At this point, it is typically necessary to apply pressure to the catheter to keep blood from flowing through the catheter.

After the needle has been removed the hub of the catheter is affixed to the skin of the patient at the intravascular site. During this procedure, the healthcare provider typically holds the hub of the intravascular catheter to the site of insertion with one hand and with his or her free hand retrieves one piece of previously torn tape and slips it adhesive side up underneath the hub of the catheter. The healthcare provider then pulls one free end of the tape over the catheter hub and wraps it over the catheter hub to stick the adhesive to the patient's skin. Then, the healthcare provider wraps the other end of the tape over the opposite side of the catheter hub and sticks it to the patient's skin. The intravenous tubing line is then connected to the catheter hub and the tourniquet is released. At this point, additional strips of tape can be used to more firmly adhere the catheter to the intravascular site. Then, a clear occlusive dressing is placed over the top of the intravascular site.

The biggest problem with this conventional procedure is that the tape utilized in adhering the catheter to the intravascular site can be contaminated, exposing the patient to the risk of nosocomial infection. Another inherent problem with this procedure is that the tape can get stuck to the glove of the healthcare provider. In one unfortunate scenario that occurs from time to time, the catheter can be accidentally removed from the intravascular site by virtue of being unknowingly stuck to the healthcare provider's glove. After the catheter has served its purpose, it is, of course, necessary to remove it from the patient. The removal procedure can be unpleasant and can cause skin irritation in certain patients. For instance, in cases where the tape adhering the intravascular catheter is firmly stuck to the skin of the patient, it is frequently necessary for the healthcare provider to dig at the ends of the tape to establish a point where the tape can be grasped for removal. This digging action can scratch or irritate the skin of patients having sensitive skin such as those with skin conditions and elderly and newborn patients.

Example 2

The procedure utilized in Comparative Example 1 for inserting a catheter into a blood vessel on the back of a patient's hand can be done utilizing the adhesive tape and procedure of this invention. In this procedure, the healthcare provider first puts on sterile gloves for both his or her protection and the protection of the patient. Then a sterile towel is placed under the patient's arm or hand. Next, a tourniquet is applied to the patient's arm. The healthcare provider then cleans and sterilizes the site where the catheter will be inserted into the patient with an antiseptic skin prep such as antiseptic swab. The antiseptic is allowed to dry. In such a procedure an integral stylet is then inserted into a blood vessel on the back of the patient's hand by utilizing the sharp needle of the stylet to puncture through the patient's skin and other tissue to allow the stylet to enter the blood vessel. The needle is then removed from the patient's body while allowing the end of the intravascular catheter to remain in the blood vessel.

At this point, it is typically necessary to apply pressure to the catheter to keep blood from flowing through the catheter. After the needle has been removed the hub of the catheter is affixed to the skin of the patient at the intravascular site. During this procedure, the healthcare provider typically holds the hub of the intravascular catheter to the site of insertion with one hand and with his or her free hand removes the third removable cover affixed to the central portion of the adhesive side of the strip of tape. After the adhesive is exposed, the central portion of the adhesive tape is slipped with the adhesive side up underneath the hub of the catheter. The healthcare provider then removes the removal cover affixed to one end of the adhesive tape of this invention, pulls that end of the tape over the catheter hub and wraps it over the catheter hub to stick the adhesive to the patient's skin. Then, the healthcare provider removes the removable cover from the other end and wraps that end of the tape over the opposite side of the catheter hub and sticks it to the patient's skin. The intravenous tubing line is then connected to the catheter hub and the tourniquet is released. Then, a clear occlusive dressing is placed over the top of the intravascular site.

Optionally, the healthcare provider can further secure the intravascular catheter to the patient's skin by applying a second adhesive tape of this invention to the catheter at the point where it comes out from under the clear occlusive dressing. This is done by first removing the cover from the central portion of the adhesive side of the adhesive tape of this invention. The exposed adhesive is then gently pushed onto the top of the catheter at the point where it exits the clear occlusive dressing. Then, the cover is removed from one of the ends of the adhesive tape and the exposed adhesive is gently pushed into contact with the clear occlusive dressing and the patient's skin. Subsequently, the cover is removed from the other end of the adhesive tape and it is then gently pushed into contact to adhere to the clear occlusive dressing and the patient's skin.

The benefits associated with utilizing the adhesive tape of this invention include easy application with one hand with minimized risk of the tape accidentally sticking to the gloves of a healthcare provider. This accordingly reduces the risk of the catheter being accidentally pulled out of the patient due to it being accidentally stuck to the glove of the healthcare provider. Since it can be easily used while wearing gloves it also reduces the temptation of healthcare providers performing all or part of the procedure with bare hands which reduces the risk of infection for both the healthcare provider and the patient. Thus, catheters can be firmly secured to an intravascular site without the risk of contamination. The risk of the hub or tape becoming contaminated by contact with foreign objects is virtually eliminated. Aseptic techniques are utilized during the entire procedure of affixing the catheter to the intravascular site with sterility preferably being maintained.

After the catheter has served its purpose, it is, of course, necessary to remove it from the patient. The adhesive tape of this invention can be easily removed from patients in a more pleasant manner that causes less skin irritation. This is because the adhesive tape of this invention includes non-adhesive end portions or tabs that allow the healthcare provider to firmly grasp the adhesive tape for removal from the patient's skin without the need to dig at the ends of the tape to establish a point where the tape can be grasped for removal. This makes the removal procedure easier and faster for the healthcare provider. More importantly, it eliminates the need for the healthcare provider to dig at the ends or sides of the tape which greatly reduces the incidences of scratching or irritating fragile or delicate skin.

Example 3

The procedure utilized in Comparative Example 1 for inserting a catheter into a blood vessel on the back of a patient's hand can be done utilizing a sterile intravascular start kit that includes the adhesive tape of this invention. In such a procedure, the healthcare provider opens the sterile intravascular start kit and dons the sterile gloves that are packaged in the kit. Then a sterile towel is removed from the kit and placed under the patient's arm or hand.

Next, a sterile tourniquet is taken from the kit and applied to the patient's arm. The healthcare provider then removes an antiseptic skin prep, such as an antiseptic swab, from the kit and used it to clean and sterilize the site where the catheter will be inserted into the back of the patient's hand. The antiseptic is then allowed to dry. In such a procedure an integral stylet is then inserted into a blood vessel on the back of the patient's hand by utilizing the sharp needle of the stylet to puncture through the patient's skin and other tissue to allow the stylet to enter the blood vessel. The needle is then removed from the patient's body while allowing the end of the intravascular catheter to remain in the blood vessel.

At this point, it is typically necessary to apply pressure to the catheter to keep blood from flowing through the catheter. After the needle has been removed the hub of the catheter is affixed to the skin of the patient at the intravascular site. During this procedure, the healthcare provider typically holds the hub of the intravascular catheter to the site of insertion with one hand and with his or her free hand removes the sterile adhesive tape of this invention from the kit. The healthcare provider then removes the third removable cover affixed to the central portion of the adhesive side of the strip of tape with his or her free hand. After the adhesive is exposed, the central portion of the adhesive tape is slipped with the adhesive side up underneath the hub of the catheter. The healthcare provider then removes the removal cover affixed to one end of the adhesive tape of this invention then pulls that end of the tape over the catheter hub and wraps it over the catheter hub to stick the adhesive to the patient's skin. Then, the healthcare provider removes the removable cover from the other end and then wraps that end of the tape over the opposite side of the catheter hub and sticks it to the patient's skin. The intravenous tubing line is then connected to the catheter hub and the tourniquet is released. Then, a clear occlusive dressing is placed over the top of the intravascular site.

Optionally, the healthcare provider can remove a second sterile adhesive tape from the kit and further secure the intravascular catheter to the patient's skin by applying it to the catheter at the point where it comes out from under the clear occlusive dressing. This is done by first removing the cover from the central portion of the adhesive side of the adhesive tape of this invention. The exposed adhesive is then gently pushed onto the top of the catheter at the point where it exits the clear occlusive dressing. Then, the cover is removed from one of the ends of the adhesive tape and the exposed adhesive is gently pushed into contact with the clear occlusive dressing and the patient's skin. Subsequently, the cover is removed from the other end of the adhesive tape and it is then gently pushed into contact to adhere to the clear occlusive dressing and the patient's skin.

The most significant benefits associated with utilizing the sterile intravascular start kit of this invention include convenience, ease of use, and reduced risk of contamination. Because the sterile intravascular start kit includes at least one sterile adhesive tape of this invention a catheter can be easily affixed to an intravascular site with one hand with minimized risk of the tape accidentally sticking to the gloves of a healthcare provider. This accordingly reduces the risk of the catheter being accidentally pulled out of the patient due to it being accidentally stuck to the glove of the healthcare provider. Since it can be easily used while wearing gloves it also reduces the temptation of healthcare providers performing all or part of the procedure with bare hands which reduces the risk of infection for both the healthcare provider and the patient. Thus, catheters can be firmly secured to an intravascular site without the risk of contamination. The risk of the hub or tape becoming contaminated by contact with foreign objects is virtually eliminated. During the entire procedure of affixing the catheter to the intravascular site sterility is maintained.

After the catheter has served its purpose, it is, of course, necessary to remove it from the patient. The adhesive tape of this invention can be easily removed from patients in a more pleasant manner that causes less skin irritation. This is because the adhesive tape of this invention includes non-adhesive end portions or tabs that allow the healthcare provider to firmly grasp the adhesive tape for removal from the patient's skin without the need to dig at the ends of the tape to establish a point where the tape can be grasped for removal. This makes the removal procedure easier and faster for the healthcare provider. More importantly, it eliminates the need for the healthcare provider to dig at the ends or sides of the tape which greatly reduces the incidences of scratching or irritating fragile or delicate skin.

While certain representative embodiments and details have been shown for the purpose of illustrating the subject invention, it will be apparent to those skilled in this art that various changes and modifications can be made therein without departing from the scope of the subject invention.

What is claimed is:

1. An adhesive tape to secure an intravascular catheter having a hub to the skin of a patient at an intravascular site by adhering the tape to the hub and to the skin of the patient comprising: (a) a solid strip of tape having adhesive on all of one side except for portions at the ends, the strip of tape having a length of 50 mm to 150 mm and width of about 4 to 25 mm; (b) two removable covers affixed near the ends of the adhesive side of the strip, wherein the removable covers include cover tabs, wherein the removable covers are separated from each other by a centrally located portion of the strip of tape, wherein the two removable covers affixed near the ends of the adhesive side of the strip do not overhang the sides of the strip, wherein the centrally located portion of the strip of the tape is between 2% and 33% of the overall length of the tape, and wherein the centrally located portion of the strip is adapted for adhering the hub to the skin of the patient; and (c) a third removable cover affixed to the central portion of the adhesive side of the strip of tape, wherein the third removable cover is affixed to the adhesive on the adhesive side of the strip of tape, and wherein the third removable cover extends completely over the cover tabs, wherein the third removable cover extends only partially over the removable covers, wherein the third removable cover does not overhang the sides of the strip, wherein the cover tabs extend away from the adhesive, and wherein the cover tabs are shorter than the removable covers.

2. An adhesive tape for an intravascular catheter as specified in claim 1 wherein the width of the two removable covers affixed near the ends of the adhesive side of the strip is the same as the width of the strip.

3. An adhesive tape for an intravascular catheter as specified in claim 1 wherein the centrally located portion of the strip of the tape is between 10% and 20% of the overall length of the tape.

4. An adhesive tape for an intravascular catheter as specified in claim 3 wherein the tape has a width which is within the range of 5 mm to 10 mm.

5. An adhesive tape to secure an intravascular catheter having a hub to the skin of a patient at an intravascular site by adhering the tape to the hub and to the skin of the patient comprising: (a) a solid strip of tape having adhesive on all of one side, wherein the adhesive side of the strip of tape has non-removable covers covering the adhesive at each of its ends, the strip of tape having a length of 50 mm to 150 mm and width of about 4 to 25 mm; (b) two removable covers affixed near the ends of the adhesive side of the strip, wherein the removable covers include cover tabs, wherein the removable covers are separated from each other by a centrally located portion of the strip of tape, wherein the two removable covers affixed near the ends of the adhesive side of the strip do not overhang the sides of the strip, wherein the centrally located portion of the strip of the tape is between 2% and 33% of the overall length of the tape, and wherein the centrally located portion of the strip is adapted for adhering the hub to the skin of the patient; and (c) a third removable cover affixed to the central portion of the adhesive side of the strip of tape, wherein the third removable cover is affixed to the adhesive on the adhesive side of the strip of tape, and wherein the third removable cover extends completely over the cover tabs, wherein the third removable cover extends only partially over the removable covers, wherein the third removable cover does not overhang the sides of the strip, wherein the cover tabs extend away from the adhesive, and wherein the cover tabs are shorter than the removable covers.

6. An adhesive tape for an intravascular catheter as specified in claim 5 wherein the width of the two removable covers affixed near the ends of the adhesive side of the strip is the same as the width of the strip.

7. An adhesive tape for an intravascular catheter as specified in claim 6 wherein the centrally located portion of the strip of the tape is between 10% and 20% of the overall length of the tape.

* * * * *